United States Patent
Nappa et al.

(10) Patent No.: US 7,500,968 B1
(45) Date of Patent: Mar. 10, 2009

(54) UNIDIRECTIONAL URINE COLLECTION RESERVOIR

(76) Inventors: Thomas P. Nappa, 166 Oakhurst Ave., Warwick, RI (US) 02889; Michael J. Nappa, 207 Richmond Dr., Warwick, RI (US) 02888

( * ) Notice: Subject to any disclaimer, the term of this patent is extended or adjusted under 35 U.S.C. 154(b) by 374 days.

(21) Appl. No.: 11/368,122

(22) Filed: Mar. 6, 2006

(51) Int. Cl.
*A61F 5/44* (2006.01)
(52) U.S. Cl. ............... 604/349; 604/315; 604/318; 604/319; 604/320; 604/321; 604/322; 604/323; 604/324; 604/325; 604/350; 137/15.22; 137/247.21; 137/519.5; 137/533.11; 251/166; 251/315.01; 251/315.1
(58) Field of Classification Search ......... 604/317–325, 604/349
See application file for complete search history.

(56) References Cited

U.S. PATENT DOCUMENTS

| | | | |
|---|---|---|---|
| 3,298,370 A * | 1/1967 | Beatty | 604/350 |
| 3,440,470 A * | 4/1969 | Decker | 313/103 R |
| 3,605,749 A * | 9/1971 | Heimlich | 604/247 |
| 3,739,783 A | 6/1973 | Broerman | |
| 4,189,789 A * | 2/1980 | Hofstetter | 4/144.1 |
| 4,526,576 A * | 7/1985 | Cianci | 604/322 |
| 4,588,397 A | 5/1986 | Giacalone | |
| 4,625,734 A * | 12/1986 | Sherlock et al. | 600/575 |
| 4,840,625 A | 6/1989 | Bell | |
| 5,022,422 A * | 6/1991 | di Palma | 137/15.18 |
| 5,295,979 A | 3/1994 | DeLaurentis et al. | |
| D358,468 S | 5/1995 | Howard | |
| 5,616,138 A * | 4/1997 | Propp | 604/317 |
| 5,624,374 A * | 4/1997 | Von Iderstein | 600/29 |
| D418,918 S | 1/2000 | Cunningham | |
| 6,050,934 A * | 4/2000 | Mikhail et al. | 600/30 |
| 6,068,618 A | 5/2000 | Anderson | |

* cited by examiner

*Primary Examiner*—Tatyana Zalukaeva
*Assistant Examiner*—Ilya Y Treyger

(57) ABSTRACT

A urine collection apparatus includes an adaptable reservoir that is sized and shaped for conveniently and effectively being transported by a user. The reservoir includes a top portion including an intake valve in fluid communication with the reservoir. The intake valve is provided with an opening such that the male catheter can be selectively biased in fluid communication with an interior of the reservoir. Such an intake valve further has a threaded screw cap directly and adjustably coupled thereto for effectively allowing a selected quantity of air to continuously flow into and out of the reservoir wherein the quantity of air is commensurate with a quantity of fluid discharging and entering the reservoir respectively. The intake valve preferably has a monolithically formed conical tip that terminates proximal to the top portion such that the male catheter can effectively be supported at a fixed relationship with the reservoir during operating conditions.

12 Claims, 3 Drawing Sheets

UNIDIRECTIONAL URINE COLLECTION RESERVOIR

CROSS REFERENCE TO RELATED APPLICATIONS

Not Applicable.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to colostomy bags for males and, more particularly, to a unidirectional urine collection reservoir.

2. Prior Art

The inability of a person to control the flow of urine results from a number of different medical conditions, particularly conditions associated with advanced age. Also, in certain cases, a patient for medical treatment may not necessarily be incontinent, but may be immobile or otherwise unable to relieve himself normally. In these situations, it is desirable to provide some means of urine collection.

A number of external catheter systems have been devised for urine drainage for incontinent males. In systems where the catheter was attached to the skin of the penile shaft, either directly by an adhesive coating, or indirectly through an adhesive band, the fit between the penis and the catheter sheath material had to be tight at all times in order to prevent leakage. Furthermore, the fit had to be tight to prevent the catheter sheath from coming off during large flows of urine.

However, if the fit between the penis and the catheter sheath was too tight, the sheath often caused pain or discomfort to the patient generally, and also caused edema, inflammation, and chafing. The problem was further exacerbated during involuntary erections. Furthermore, adhesive coated external catheter sheaths were difficult to apply.

Problems also arose with external catheter systems. The collar had to fit tightly to prevent leakage, but if it was too tight, it caused discomfort generally and particularly during involuntary erections. Furthermore, the briefs had to be positioned carefully on the patient and therefore restricted the patient's movement. The briefs were also expensive to produce and greatly increased the cost of the system. As a result, none of the prior art external catheters provide a secure, yet comfortable seal and manner of attachment.

Four million urinary catheters are used yearly in the United States, and about 40 percent of patients develop urinary tract infections due to the use of the catheter. About 3.2 percent of the total number develops bacteriaemia (bacteria in the blood). Ten to twenty thousand people die each year, and about one billion dollars are expended to manage the complications arising from the use of urinary catheters and drainage systems. Clearly, any means which helps to reduce such infections may have a significant effect on the overall cost of medical services.

Accordingly, a need remains for a urine collection apparatus to overcome the above-noted shortcomings. The present invention satisfies such a need by providing a unidirectional urine collection reservoir for use with a male catheter. Such a reservoir may be used with either a straight catheter or indwelling catheter (as a urine collection pouch), increasing its versatility and usefulness. Such a catheter eliminates soiled linens, uncomfortable patient contact with wetness, odor, and the opportunity for secondary infection. The present invention is easy to use, increases patient comfort, and makes hospital attendants more effective and efficient in their work.

BRIEF SUMMARY OF THE INVENTION

In view of the foregoing background, it is therefore an object of the present invention to provide an apparatus for collecting urine. These and other objects, features, and advantages of the invention are provided by an apparatus for collecting and dispensing urine received via a male catheter.

The apparatus includes an adaptable reservoir that is sized and shaped for conveniently and effectively being transported by a user. Such a reservoir includes a top portion including an intake valve in fluid communication with the reservoir. The intake valve is provided with an opening such that the male catheter can be selectively biased in fluid communication with an interior of the reservoir. Such an intake valve further has a threaded screw cap directly and adjustably coupled thereto for effectively allowing a selected quantity of air to continuously flow into and out of the reservoir wherein the quantity of air is commensurate with a quantity of fluid discharging and entering the reservoir respectively. The intake valve preferably has a monolithically formed conical tip that terminates proximal to the top portion such that the male catheter can effectively be supported at a fixed relationship with the reservoir during operating conditions.

The reservoir includes a first handle for conveniently hanging the reservoir on a bed or chair. Such a first handle is pivotal between raised and lowered positions for advantageously and effectively conforming to an outer contour of the reservoir as desired by the user. The reservoir is formed from flexible and non-corrosive material wherein the reservoir has an outer surface provided with surface indicia for advantageously and conveniently assisting a care giver to visually detect a volume of urine collected therein.

The reservoir preferably further includes a second handle that has an inverted U-shape provided with one end directly coupled to the reservoir. Such a second handle includes an eyelet that is directly mated to an apex thereof such that the male catheter can conveniently be guided therethrough and advantageously be maintained at a substantially stable position during operating conditions. A third arcuately shaped handle has opposed ends pivotally coupled directly to lateral sides of the top region.

Such a reservoir also includes an exit valve in fluid communication with a lower portion of the reservoir and is situated subjacent to the intake valve. The exit valve protrudes outwardly from the reservoir outer surface. Such an exit valve may include first, second and third sections that are removably attachable to each other in such a manner that fluid is effectively allowed to exit through the exit valve with the first and second sections directly coupled to each other while the third section is detached from the second section. The exit valve is provided with first and second linear bores axially channeled therethrough wherein the bores extend along a longitudinal length of the exit valve. Such an exit valve may further be provided with a spherical ball valve nested between the first and second sections. The ball valve advantageously and effectively prohibits fluid from passing beyond the first bore when the ball valve maintains continuous medial contact between the first and second sections.

Said exit valve includes first, second and third sections removably attachable to each other in such a manner that fluid is allowed to exit through said exit valve while said second and third sections are directly coupled to each other and said second section is separated from said ball valve, said exit valve being provided with first and second linear bores axially channeled therethrough wherein the bores extends along a longitudinal length of said exit valve.

The first section of the exit valve may be threadably and removably conjoined directly to a bottom edge of the reservoir. Such a first section includes a cavity formed at a distal end of the first bore for housing the ball valve therein. The second section of the exit valve has a planar proximal face directly abutted against the ball valve such that the ball valve effectively prevents fluids from entering the second bore when the second section is fully mated to the first section and beyond a predetermined threshold. The proximal end has a threaded outer surface threadably coupled to a threaded inner surface of the first section. The third section defines an end cap provided with a planar proximal face directly plugged against a distal end of the second bore such that the fluid is advantageously and effectively prohibited from exiting the second section when the end cap is engaged with the second bore. Such a third section is threadably removable from the second section.

The reservoir further includes a top region formed from rigid plastic material. Such a top region has a fixed shape for effectively anchoring the first handle. A lower region has arcuately shaped lateral sides that are suitably sized and shaped for directly abutting against a curvilinear contour of a user's abdomen during operating conditions.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

Figure 1:
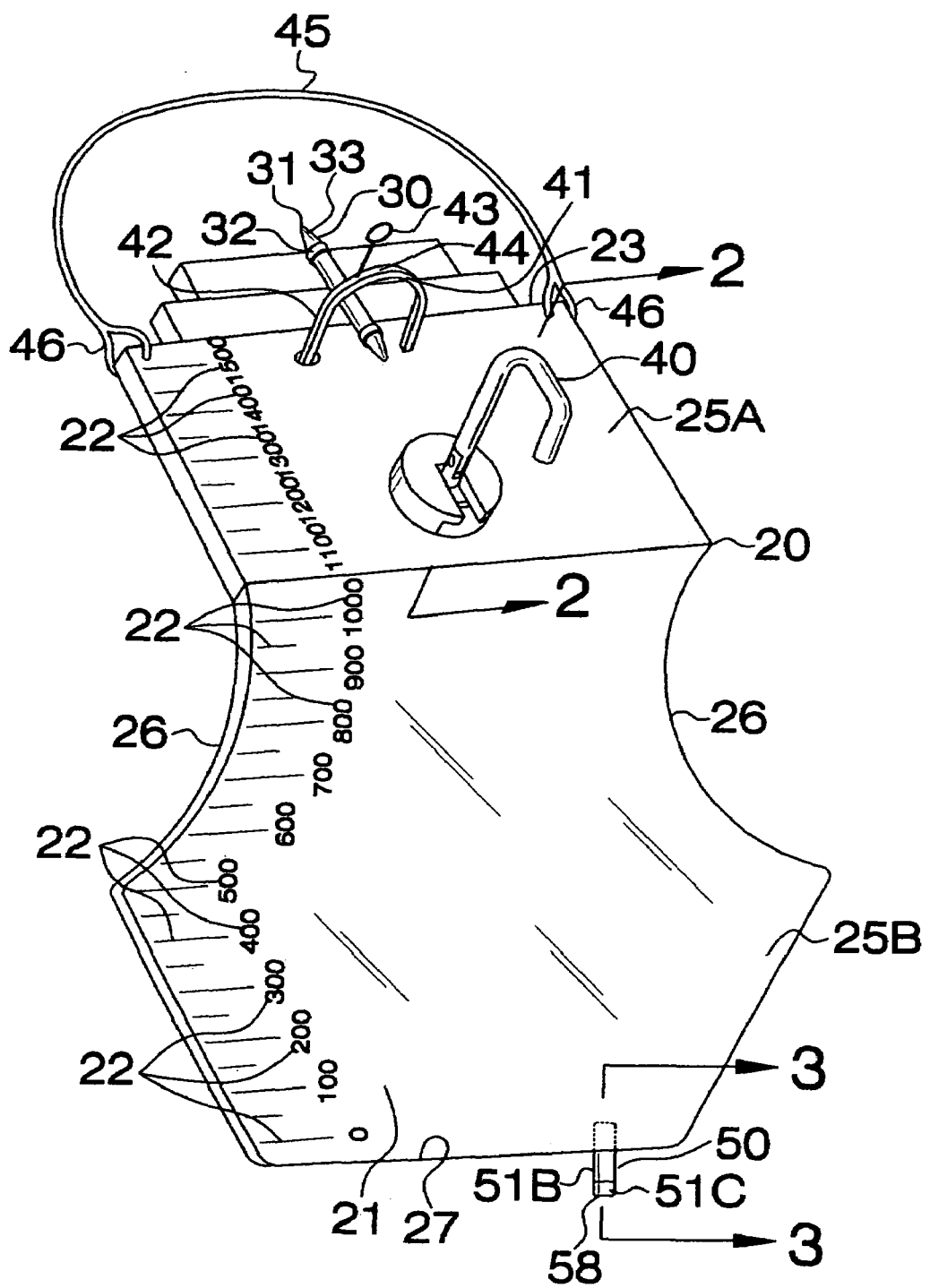
FIG. 1 is a perspective view of a unidirectional urine collection apparatus, in accordance with the present invention.
Figure 2:
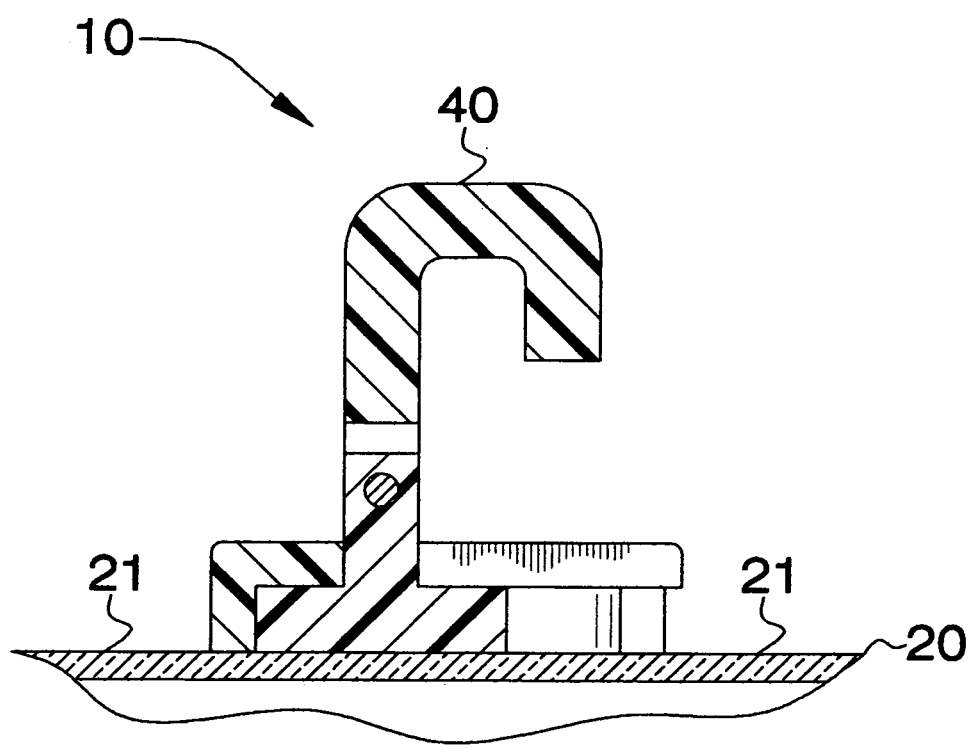
FIG. 2 is a cross-sectional view of the first handle shown in FIG. 1, taken along line 2-2.
Figure 3:
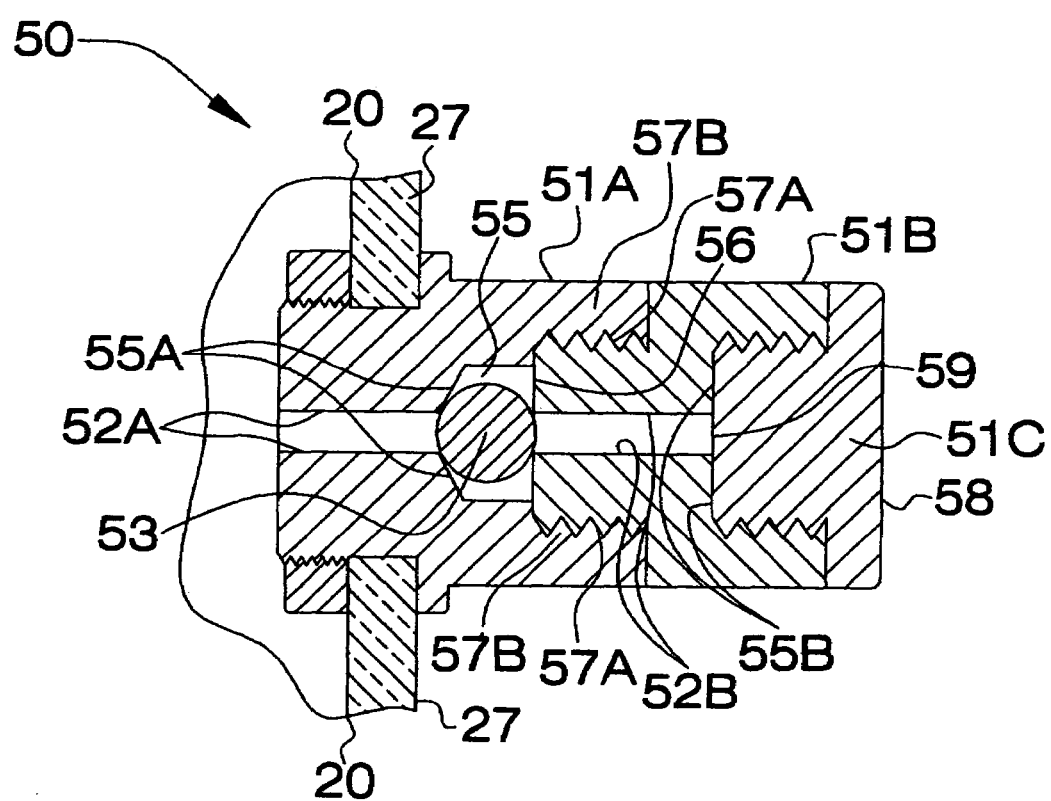
FIG. 3 is a cross-sectional view of the exit valve shown in FIG. 1, taken along line 3-3.

The apparatus of this invention is referred to generally in FIGS. 1-3 by the reference numeral 10 and is intended to provide a urine collection apparatus for receiving and dispensing urine received via a male catheter. It should be understood that the apparatus 10 may be used to collect and dispense many different types of fluid and should not be limited to only urine.

Initially referring to FIGS. 1 and 3, the apparatus 10 includes an adaptable reservoir 20 that is sized and shaped for conveniently and effectively being transported by a user. Such a reservoir 20 is formed from flexible and non-corrosive material wherein the reservoir 20 has an outer surface 21 provided with surface indicia 22 that are vital for advantageously and conveniently assisting a care giver to visually detect a volume of urine collected therein. Thus, the caregiver has a visual cue to determine when the reservoir 20 should be emptied before it becomes too heavy and uncomfortable. Such indicia 22 are also important to the caregiver because hospital and nursing home staff must often closely monitor the amount of urine generated by a patient in order to determine the effectiveness of the patient's medication. This is particularly true for patients experiencing a build-up of fluid in their lungs and/or lower appendages that must be closely watched. The reservoir 20 includes a top portion 23 including an intake valve 30 in fluid communication with the reservoir 30. Of course, such an apparatus 10 may further include a flexible carrying cord (not shown) attached to the top portion 23 so that a user or care giver may readily and easily transport the apparatus 10 when the user desires to move about.

Referring to FIG. 1, the reservoir 20 further includes a top region 25A formed from rigid plastic material. Such a top region 25A has a fixed shape for effectively anchoring the first handle 40 (described herein below). A lower region 25B has arcuately shaped lateral sides 26 that are suitably sized and shaped for directly abutting, without the use of intervening elements, against a curvilinear contour of a user's abdomen during operating conditions, which is critical for affording a maximum level of comfort to the patient.

Again referring to FIG. 1, the intake valve 30 is provided with an opening 31 such that the male catheter can be selectively biased in fluid communication with an interior of the reservoir 20. The intake valve 30 further has a threaded screw cap 32 directly and adjustably coupled thereto, without the use of intervening elements, which is crucial for effectively allowing a selected quantity of air to continuously flow into and out of the reservoir 20 wherein the quantity of air is commensurate with a quantity of fluid discharging and entering the reservoir 20 respectively. Such an intake valve 30 also has a monolithically formed conical tip 33 that terminates proximal to the top portion 23, which is essential such that the male catheter can effectively be supported at a fixed relationship with the reservoir 20 during operating conditions. Reduced movement of the attached catheter will advantageously and effectively result in an increased level of comfort for the patient.

Referring to FIGS. 1 and 2, the reservoir 20 includes a first handle 40 that is important for conveniently hanging the reservoir 20 on a bed or chair. Of course, the first handle 40 may be used to suspend the reservoir 20 from other suitable surfaces as well, as is obvious to a person of ordinary skill in the art. Such a first handle 40 is pivotal between raised and lowered positions for advantageously and effectively conforming to an outer contour of the reservoir 20 as desired by the user. The reservoir 20 further includes a second handle 41 that has an inverted U-shape provided with one end 42 directly coupled, without the use of intervening elements, to the reservoir 20. Such a second handle 41 includes an eyelet 43 that is directly mated, without the use of intervening elements, to an apex 44 thereof, which is essential such that the male catheter can conveniently be guided therethrough and advantageously be maintained at a substantially stable position during operating conditions. The eyelet 43 is an important feature for ensuring that the movement of the catheter is limited, resulting in increased patient comfort, while also preventing any conduits attached to the catheter from becoming twisted and blocked, which would prevent the free flow of fluids therethrough. A third arcuately shaped handle 45 has opposed ends 46 pivotally coupled directly, without the use of intervening elements, to lateral sides 24 of the top region (described herein below).

Referring to FIGS. 1 and 3, such a reservoir 20 also includes an exit valve 50 that is in fluid communication with a lower portion 25B of the reservoir 20 and is situated subjacent to the intake valve 30. The exit valve 50 protrudes outwardly from the reservoir outer surface 21. Such an exit valve 50 includes first 51A, second 51B and third 51C sections that are removably attachable to each other in such a manner that fluid is effectively allowed to exit through the exit valve 50 with the first 51A and second 51B sections directly coupled, without the use of intervening elements, to each other while the third section 51C is detached from the second section 51B. The exit valve 50 is provided with first 52A and second 52B linear bores axially channeled therethrough wherein the bores 52 extend along a longitudinal length of the exit valve 50. Such an exit valve 50 is further provided with a spherical ball valve 53 nested between the first 51A and second 51B sections. The ball valve 53 advantageously and effectively prohibits fluid from passing beyond the first bore 52A when the ball valve 53 maintains continuous medial contact between the first 51A and second 51B sections. This is an essential feature for increasing patient comfort and preventing soiled linens and patient gowns. Such a feature also promotes cleanliness, thereby improving the sanitary condition of a hospital room, which is crucial for reducing the occurrence of secondary viral and bacterial infections.

Still referring to FIGS. 1 and 3, the first section 51A of the exit valve 50 is threadably and removably conjoined directly, without the use of intervening elements, to a bottom edge 27 of the reservoir 20. Such a first section 51 includes a cavity 54 formed at a distal end 55A of the first bore 52A for housing the ball valve 53 therein. The second section 51B of the exit valve 50 has a planar proximal face 56 directly abutted, without the use of intervening elements, against the ball valve 53, which is a crucial feature such that the ball valve 53 effectively prevents fluids from entering the second bore 52B when the second section 51B is fully mated to the first section 51A and beyond a predetermined threshold. The proximal end 56 has a threaded outer surface 57A threadably coupled to a threaded inner surface 57B of the first section 51A. The third section 51C defines an end cap 58 provided with a planar proximal face 59 directly plugged, without the use of intervening elements, against a distal end 55B of the second bore 52B such that the fluid is advantageously and effectively prohibited from exiting the second section 51B when the end cap 58 is engaged with the second bore 52B. Such a third section 51C is threadably removable from the second section 51B.

In use, the apparatus 10 offers a true closed system that reduces the opportunity for infection. The large size of the apparatus 10 allows it to be used by in-dwelling catheter patients as a urine collection pouch for added convenience. The apparatus 10 further increases the efficiency of medical care providers, resulting in enhanced patient care, and providing greater patient self-esteem, comfort, and dignity.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. An apparatus for collecting and dispensing urine received via a male catheter, said apparatus comprising:
   an adaptable reservoir sized and shaped for being transported by a user, said reservoir including a top portion comprising an intake valve in fluid communication with said reservoir, said intake valve being provided with an opening such that the male catheter can be selectively biased in fluid communication with an interior of said reservoir, said valve having a threaded screw cap directly and adjustably coupled thereto for allowing a selected quantity of air to continuously flow into and out of said reservoir wherein the quantity of air is commensurate with a quantity of fluid discharging and entering said reservoir respectively, said reservoir further comprising a first handle for hanging said reservoir on a bed or chair, said first handle being pivotal between raised and lowered positions for conforming to an outer contour of said reservoir as desired by the user, said reservoir being formed from flexible and non-corrosive material wherein said reservoir has an outer surface provided with surface indicia for assisting a care giver to visually detect a volume of urine collected therein, said reservoir further including an exit valve in fluid communication with a lower portion of said reservoir and being situated subjacent said intake valve, said exit valve protruding outwardly from said reservoir outer surface;
   wherein said exit valve is provided with an a spherical ball valve nested between said first and second sections, said ball valve prohibiting fluid from passing beyond said first bore when said ball valve maintain continuous medial contact between said first and second sections;
   wherein said exit valve includes first, second and third sections removably attachable to each other in such a manner that fluid is allowed to exit through said exit valve while said second and third sections are directly coupled to each other and said second section is separated from said ball valve, said exit valve being provided with first and second linear bores axially channeled therethrough wherein the bores extends along a longitudinal length of said exit valve.

2. The apparatus of claim 1, wherein said intake valve has a monolithically formed conical tip terminating proximal to said top portion such that the male catheter can be effectively supported at a fixed relationship with said reservoir during operating conditions.

3. The apparatus of claim 1, wherein said reservoir further comprises:
   a second handle having an inverted U-shape provided with one end directly coupled to said reservoir, said second handle including an eyelet directly mated to an apex thereof such that the male catheter can be guided therethrough and maintained at a substantially stable position during operating conditions.

4. The apparatus of claim 1, wherein said first section of said exit valve is threadably and removably conjoined directly to a bottom edge of said reservoir, said first section including a cavity formed at a distal end of said first bore for housing said ball valve therein, said second section of said exit valve having a planar proximal face directly abutted against said ball valve such that said ball valve prevents fluids from entering said second bore when said second section is fully mated to said first section and beyond a predetermined threshold, said proximal end having a threaded outer surface threadably coupled to a threaded inner surface of said first section, said third section defining an end cap provided with a planar proximal face directly plugged against a distal end of said second bore such that the fluid is prohibited from exiting said second section when said end cap is engaged with said second bore, said third section being threadably removable from said second section.

5. An apparatus for collecting and dispensing urine received via a male catheter, said apparatus comprising:
  an adaptable reservoir sized and shaped for being transported by a user, said reservoir including a top portion comprising an intake valve in fluid communication with said reservoir, said intake valve being provided with an opening such that the male catheter can be selectively biased in fluid communication with an interior of said reservoir, said valve having a threaded screw cap directly and adjustably coupled thereto for allowing a selected quantity of air to continuously flow into and out of said reservoir wherein the quantity of air is commensurate with a quantity of fluid discharging and entering said reservoir respectively, said reservoir further comprising a first handle for hanging said reservoir on a bed or chair, said first handle being pivotal between raised and lowered positions for conforming to an outer contour of said reservoir as desired by the user, said reservoir being formed from flexible and non-corrosive material wherein said reservoir has an outer surface provided with surface indicia for assisting a care giver to visually detect a volume of urine collected therein, said reservoir further including an exit valve in fluid communication with a lower portion of said reservoir and being situated subjacent said intake valve, said exit valve protruding outwardly from said reservoir outer surface;
  a top region formed from rigid plastic material, said top region having a fixed shape for anchoring said first and second handles; and
  a third arcuately shaped handle having opposed ends pivotally coupled directly to lateral sides of said top region;
  wherein said exit valve is provided with an a spherical ball valve nested between said first and second sections, said ball valve prohibiting fluid from passing beyond said first bore when said ball valve maintain continuous medial contact between said first and second sections;
  wherein said exit valve includes first, second and third sections removably attachable to each other in such a manner that fluid is allowed to exit through said exit valve while said second and third sections are directly coupled to each other and said second section is separated from said ball valve, said exit valve being provided with first and second linear bores axially channeled therethrough wherein the bores extends along a longitudinal length of said exit valve.

6. The apparatus of claim 5, wherein said intake valve has a monolithically formed conical tip terminating proximal to said top portion such that the male catheter can be effectively supported at a fixed relationship with said reservoir during operating conditions.

7. The apparatus of claim 5, wherein said reservoir further comprises:
  a second handle having an inverted U-shape provided with one end directly coupled to said reservoir, said second handle including an eyelet directly mated to an apex thereof such that the male catheter can be guided therethrough and maintained at a substantially stable position during operating conditions.

8. The apparatus of claim 5, wherein said first section of said exit valve is threadably and removably conjoined directly to a bottom edge of said reservoir, said first section including a cavity formed at a distal end of said first bore for housing said ball valve therein, said second section of said exit valve having a planar proximal face directly abutted against said ball valve such that said ball valve prevents fluids from entering said second bore when said second section is fully mated to said first section and beyond a predetermined threshold, said proximal end having a threaded outer surface threadably coupled to a threaded inner surface of said first section, said third section defining an end cap provided with a planar proximal face directly plugged against a distal end of said second bore such that the fluid is prohibited from exiting said second section when said end cap is engaged with said second bore, said third section being threadably removable from said second section.

9. An apparatus for collecting and dispensing urine received via a male catheter, said apparatus comprising:
  an adaptable reservoir sized and shaped for being transported by a user, said reservoir including a top portion comprising an intake valve in fluid communication with said reservoir, said intake valve being provided with an opening such that the male catheter can be selectively biased in fluid communication with an interior of said reservoir, said valve having a threaded screw cap directly and adjustably coupled thereto for allowing a selected quantity of air to continuously flow into and out of said reservoir wherein the quantity of air is commensurate with a quantity of fluid discharging and entering said reservoir respectively, said reservoir further comprising a first handle for hanging said reservoir on a bed or chair, said first handle being pivotal between raised and lowered positions for conforming to an outer contour of said reservoir as desired by the user, said reservoir being formed from flexible and non-corrosive material wherein said reservoir has an outer surface provided with surface indicia for assisting a care giver to visually detect a volume of urine collected therein, said reservoir further including an exit valve in fluid communication with a lower portion of said reservoir and being situated subjacent said intake valve, said exit valve protruding outwardly from said reservoir outer surface;
  a top region formed from rigid plastic material, said top region having a fixed shape for anchoring said first and second handles;
  a third arcuately shaped handle having opposed ends pivotally coupled directly to lateral sides of said top region; and
  a lower region having arcuately shaped lateral sides suitably sized and shaped for directly abutting against a curvilinear contour of a users abdomen during operating conditions;

wherein said exit valve is provided with an a spherical ball valve nested between said first and second sections, said ball valve prohibiting fluid from passing beyond said first bore when said ball valve maintain continuous medial contact between said first and second sections;

wherein said exit valve includes first, second and third sections removably attachable to each other in such a manner that fluid is allowed to exit through said exit valve while said second and third sections are directly coupled to each other and said second section is separated from said ball valve, said exit valve being provided with first and second linear bores axially channeled therethrough wherein the bores extends along a longitudinal length of said exit valve.

10. The apparatus of claim 9, wherein said intake valve has a monolithically formed conical tip terminating proximal to said top portion such that the male catheter can be effectively supported at a fixed relationship with said reservoir during operating conditions.

11. The apparatus of claim 9, wherein said reservoir further comprises:

a second handle having an inverted U-shape provided with one end directly coupled to said reservoir, said second handle including an eyelet directly mated to an apex thereof such that the male catheter can be guided therethrough and maintained at a substantially stable position during operating conditions.

12. The apparatus of claim 9, wherein said first section of said exit valve is threadably and removably conjoined directly to a bottom edge of said reservoir, said first section including a cavity formed at a distal end of said first bore for housing said ball valve therein, said second section of said exit valve having a planar proximal face directly abutted against said ball valve such that said ball valve prevents fluids from entering said second bore when said second section is fully mated to said first section and beyond a predetermined threshold, said proximal end having a threaded outer surface threadably coupled to a threaded inner surface of said first section, said third section defining an end cap provided with a planar proximal face directly plugged against a distal end of said second bore such that the fluid is prohibited from exiting said second section when said end cap is engaged with said second bore, said third section being threadably removable from said second section.

* * * * *